United States Patent [19]
Gammell

[11] Patent Number: 5,436,565
[45] Date of Patent: Jul. 25, 1995

[54] NON-CONTACTING CAPACITANCE PROBE FOR DIELECTRIC CURE MONITORING

[75] Inventor: Paul M. Gammell, Silver Spring, Md.

[73] Assignee: The United States of America as represented by the Secretary of the Navy, Washington, D.C.

[21] Appl. No.: 944,602

[22] Filed: Sep. 14, 1992

[51] Int. Cl.[6] ............................................. G01R 27/26
[52] U.S. Cl. ...................................... 324/679; 324/688; 324/690
[58] Field of Search ............... 324/659, 663, 671, 672, 324/679, 687, 688, 690, 677, 678

[56] References Cited

U.S. PATENT DOCUMENTS

| | | | |
|---|---|---|---|
| 3,694,742 | 9/1972 | Bergmanis et al. | 324/687 |
| 3,761,805 | 9/1973 | Dornberger | 324/677 |
| 3,781,672 | 12/1973 | Maltby et al. | 324/671 |
| 3,826,979 | 7/1974 | Steinmann | 324/688 |
| 4,723,908 | 2/1988 | Kranbuehl | 324/687 |
| 4,766,369 | 8/1988 | Weinstein | 324/671 |
| 4,817,021 | 3/1989 | Sowerby et al. | 324/687 |
| 4,845,421 | 7/1989 | Howarth et al. | 324/688 |

*Primary Examiner*—Kenneth A. Wieder
*Assistant Examiner*—Christopher M. Tobin
*Attorney, Agent, or Firm*—Jacob Shuster

[57] ABSTRACT

Conductive measuring electrodes, of a capacitive probe having a grounded guard electrode positioned therebetween shield a probe circuit, provides mutual capacitance measurements which way as a function of changes in impedance of dielectric material being monitored as it undergoes a curing process. The probe is positioned in non-embedded relation to the dielectric material to form a sensitivity region therein through which an electric field extends between the conductive measuring electrodes of the probe to establish said variable mutual capacitance measurements without extraneous influences.

6 Claims, 4 Drawing Sheets

5,436,565

NON-CONTACTING CAPACITANCE PROBE FOR DIELECTRIC CURE MONITORING

BACKGROUND OF THE INVENTION

This invention relates generally to the arrangement and operation of capacitive probes for monitoring changes in the properties of dielectric material.

The use of capacitive probes to monitor curing of dielectric materials such as epoxy resins and other plastics is generally well known. Heretofore, such probes were embedded in structural parts in which they remained or were removed, including sample parts being co-processed with other parts, as for example parts being cured in solid rocket motor environments. Questions always arise as to how representative the co-processed sample part is, such as a "witness panel" generally poured from an early or late portion of a batch which is of a smaller size and may occupy a stagnant corner of the curing oven. To avoid the problems arising in such environments, the use of capacitive probes that are not embedded in the material sample being monitored would appear to be desirable.

The use of a three terminal type of capacitive probe to sense the condition of material in which the probe electrodes are not embedded, has already been proposed as disclosed for example in U.S. Pat. Nos. 3,774,238, 3,781,672, and 3,826,979 to Hardway, Jr., Maltby et al. and Steinmann, respectively. The probe electrode arrangement as disclosed in the Hardway, Jr., patent addresses the problem of large cable capacitance as an extraneous influence without regard to material properties at a known and controlled depth to which an electric field, between the electrodes of the probe, penetrate the material. According to the Maltby, et al., patent, a probe is provided with an electrode arrangement including a guard electrode driven to the same potential as the voltage applied to a conductive measuring electrode for shielding purposes. Use of a probe electrode arrangement and support to control electric field penetration depth within the material sample being monitored, is however foreign to the disclosure in the Maltby et al., patent. As to the Steinmann patent, it discloses a probe electrode arrangement providing a signal receiver output for switch controlled operation of equipment such as a motor vehicle windshield wiper. Such output control function of the probe circuit disclosed in the Steinmann patent, is designed to detect the presence of material at a controlled distance therefrom, but not for quantification of dielectric properties of the material sample being monitored.

Accordingly, it is an important object of the present invention to provide a capacitive probe arrangement having an electrode geometry and support through which electric field penetration depth may be controlled as a function of lift-off spacing to establish a predetermined sensitivity region within the material from which monitoring measurements of material properties is made.

An additional object associated with the foregoing object is to provide a capacitive probe arrangement having measurement receiving circuitry capable of being shielded from extraneous influences as well as being insensitive to lift-off spacing between the material sample and the probe electrodes.

By virtue of the foregoing objectives, the present invention has as another object the provision of more accurate measurement and quantification of dielectric constants of dielectric material without embedding therein the probe electrodes during material cure.

SUMMARY OF THE INVENTION

In accordance with the present invention, the electrodes of one or more capacitive probe units are supported in geometric arrangements spaced by a lift-off distance from a common surface of a sample of a dielectric substance or material to monitor its properties, such as dielectric constant, during a cure process. A grounded guard electrode between two conductive measuring electrodes of each probe unit shields an associated signal receiving probe circuit from the voltage source driving one of the conductive electrodes to effect measurement of variations in mutual capacitance between the conductive electrodes reflecting changes in material properties of the material sample being monitored within a predetermined sensitivity region as determined by the electrode geometry of the probe unit and its lift-off spacing from the material sample.

According to certain embodiments of the invention, two or more probe units having different electrode geometries are interrelated by differential measurement circuitry to supply data from both of the probe units from which measurements are fed to a data processor providing material property readouts that are insensitive to lift-off spacing between the probe electrodes and the material sample being monitored. Such data processor may also be programmed to provide material property readouts insensitive to the dielectric properties of any intervening material in the lift-off spacing zone.

BRIEF DESCRIPTION OF THE DRAWING FIGURES

Other objects, advantages and novel features of the invention will become apparent from the following detailed description of the invention when considered in conjunction with the accompanying drawings wherein.

DETAILED DESCRIPTION OF PREFERRED EMBODIMENTS

Figure 1:
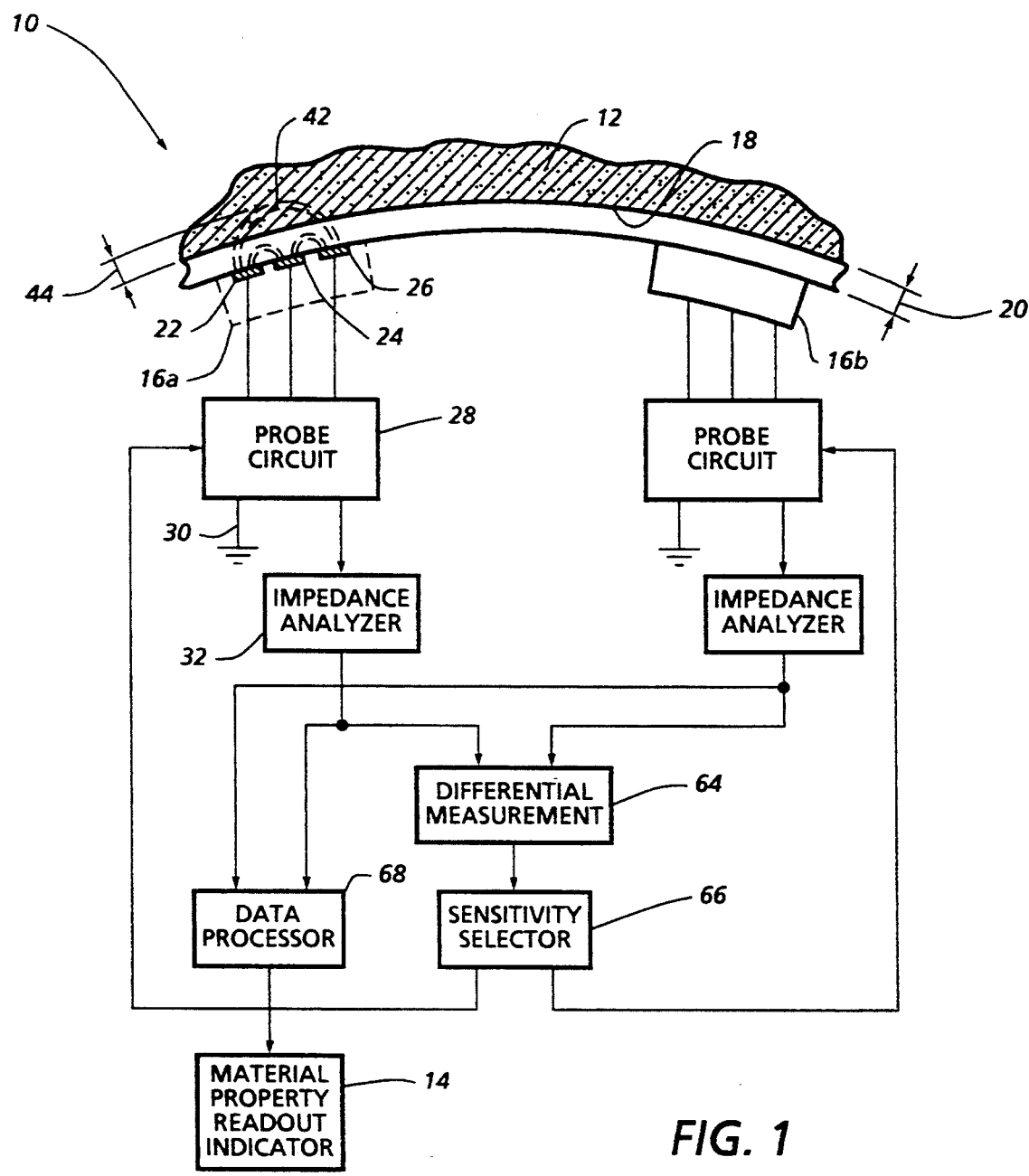
FIG. 1 is a schematic block diagram of a capacitive probe system in accordance with one embodiment of the invention.

Referring now to the drawing in detail, FIG. 1 illustrates a system generally referred to by reference numeral 10 for monitoring a dielectric material sample 12. According to one embodiment of the invention, the dielectric material of sample 12 is an epoxy or other thermosetting plastic undergoing a curing process. During such process the material in the sample 12 is monitored by providing a material property readout at indicator 14.

As shown in FIG. 1, the system 10 includes at least two probe units 16a and 16b spaced from a common continuous surface segment 18 of sample 12 by some adjusted lift-off distance 20. Each of the probe units includes at least three electrodes 22, 24 and 26 positioned in close spaced relation to each other and aligned parallel to the surface segment 18 which may be generally planar or slightly arcuate as shown. The three electrodes of each probe unit are connected to an associated probe circuit 28 having an electrically grounded terminal 30. The intermediate electrode 24 is a guard electrode connected to the ground terminal 30 as shown in FIG. 2 so as to provide shielding for its probe circuit 28 through which the mutual capacitance between conductive electrodes 22 and 26 is measured without extraneous influences.

With continued reference to FIG. 1, the mutual capacitance between the conductive electrodes 22 and 26 is measured according to one embodiment of the invention through a generally known impedance analyzer 32 connected to the probe circuit 28 having receiving inputs respectively connected to the conductive measuring electrodes 22 and 26. Thus, in response to supply of electrical energy from the probe receiver circuit to electrode 22, an electric field 42 diagrammed by field lines in FIG. 1, is established. The electric field 42 extends between the electrodes 22 and 26 to a predetermined penetration depth 44 through the dielectric material sample 12. The penetration depth of the electric field will depend on the geometry of the electrode arrangement of the probe unit and the lift-off spacing 20 of the electrodes from the material of sample 12. The electric field thus establishes a predetermined sensitivity region in the material within which measurements are made as explained hereinafter.

The mutual capacitance between electrodes 22 and 26 is made dependent exclusively on the material of sample 12 through which the electric field 42 extends by virtue of the arrangement of the present invention. Such mutual capacitance is a function of impedance or the ratio of the electrical current conducted by electrode 26 to the quadrature component of the voltage supplied to the electrode 22, while guard electrode 24 is electrically grounded. The probe receiver circuit 28 is rendered operative to provide measurements as a function of the mutual capacitance at the output of impedance analyzer 32.

Figure 2:
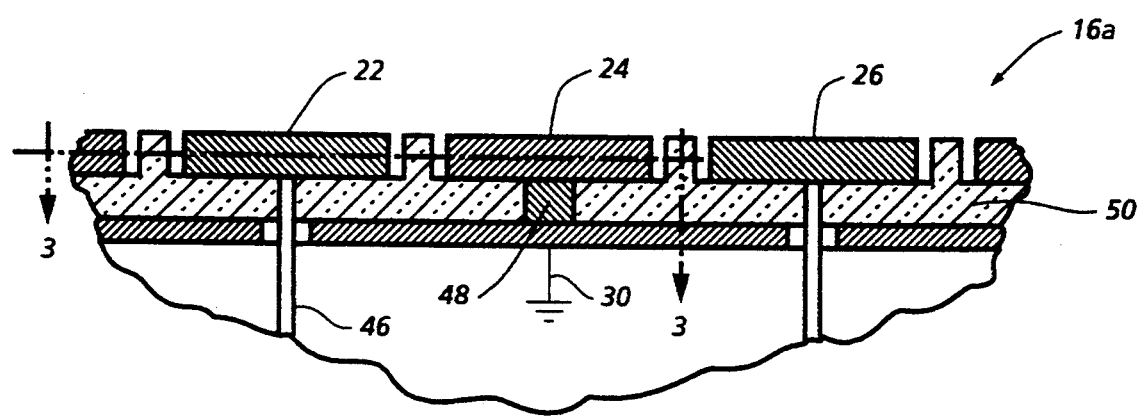
FIG. 2 is a partial simplified side section view through one of the probe units depicted in FIG. 1.
Figure 3:
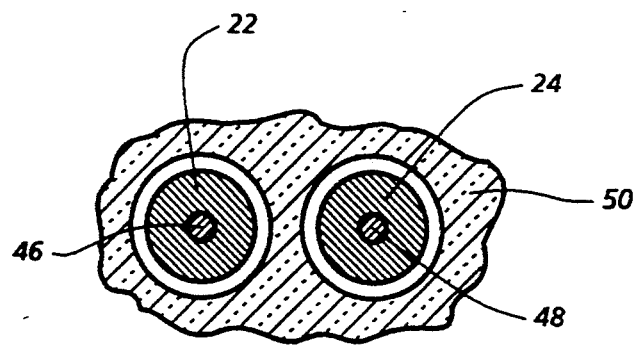
FIG. 3 is a partial section view taken substantially through a plane indicated by section line 3—3 in FIG. 2.

FIGS. 2 and 3 illustrate a geometric arrangement and support for the electrodes 22, 24 and 26 of probe unit 16a according to one specific embodiment. The electrodes are of a generally circular disc-shaped configuration, to which current conducting and grounding terminals 46 and 48 are connected, while supported on an insulating substrate 50. Based on the foregoing type of geometric electrode arrangement, the probe unit 16a was effective when driven by a voltage of 100 kHz to provide mutual capacitance measurements which varied as a function of lift-off distance 20, as depicted by curve 52 in he graph of FIG. 4. As will be noted from curve 52, a relatively wide variation range 54 for mutual capacitance occurs below a lift-off distance of 6 mm, corresponding to a depth sensitivity limit 56 for the probe unit 16a. Within the variation range 54, changes in mutual capacitance measurements will reflect readable changes in material properties suitable for monitoring the material during a curing process.

Figure 4:
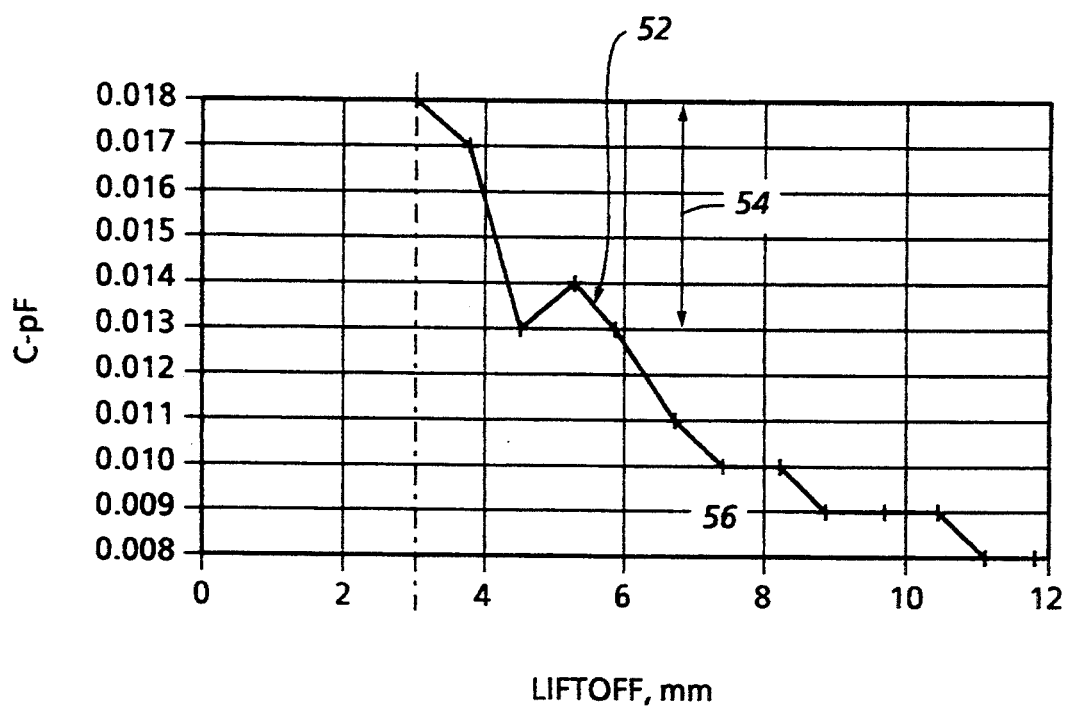
FIGS. 4 and 5 are graphs corresponding to the measurement characteristics respectively associated with the two probe units diagrammed in FIG. 1.
Figure 5:
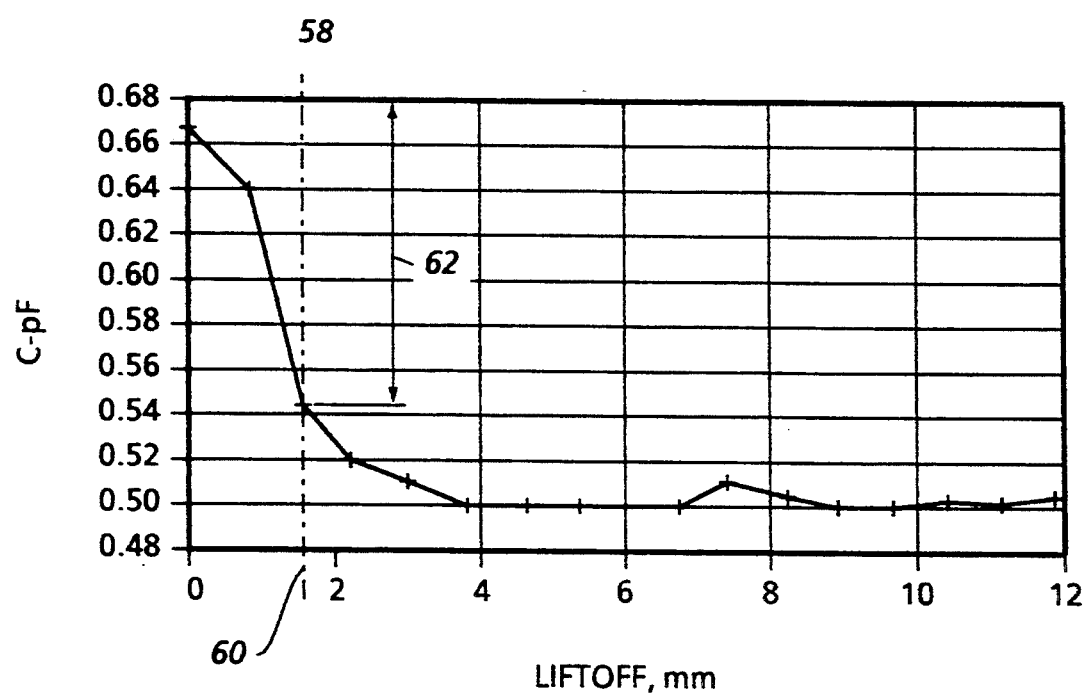

Other geometric probe electrode arrangements will provide a different relationship between mutual capacitance measurements and lift-off spacing than that graphically diagrammed in FIG. 4. For example, capacitive probe unit 16b having a generally known interdigital finger electrode arrangement will have an electric field extending-into the sample 12 to a different penetration depth and provide a mutual capacitance to lift-off relationship as depicted by curve 58 in FIG. 5. Curve 58 indicates a lower depth sensitivity limit 60 of 1.5 mm for the lift-off variation range 62 of the mutual capacitance measurements. Thus, the two probe units 16a and 16b will provide mutual capacitance measurements which fall within readable ranges 54 and 62, respectively corresponding to different ranges of sensitivity limits of 3 to 6 mm and 0 to 1.5 mm of electric field penetration. As will be apparent from curves 52 and 58 in FIGS. 4 and 5, variations in mutual capacitance measurements are significantly reduced outside of the sensitivity depth ranges.

Since the electric field penetration depth for any given lift-off distance 20 of system 10 will depend on the material being monitored, the outputs of both probe units 16a and 16b are initially applied through their probe circuits 28 and impedance analyzers 32 to a differential measurement component 64, as diagrammed in FIG. 1. By means of the output of the differential measurement component 64, a sensitivity selector 66 is rendered operative to control operation of the probe circuits 28. Thus, the outputs of the probe units are differentially weighted before application to the data processor 68 from which an accurate material property readout is obtained through readout indicator 14. The system 10 is thereby rendered selective so as to provide a material monitoring readout insensitive to lift-off spacing affecting depth penetration of the electric field. Although plural probe circuits 28 shown in FIG. 1 compensate for lift-off variations and changes in intervening materials, a single probe arrangement may suffice for many applications.

Figure 6:
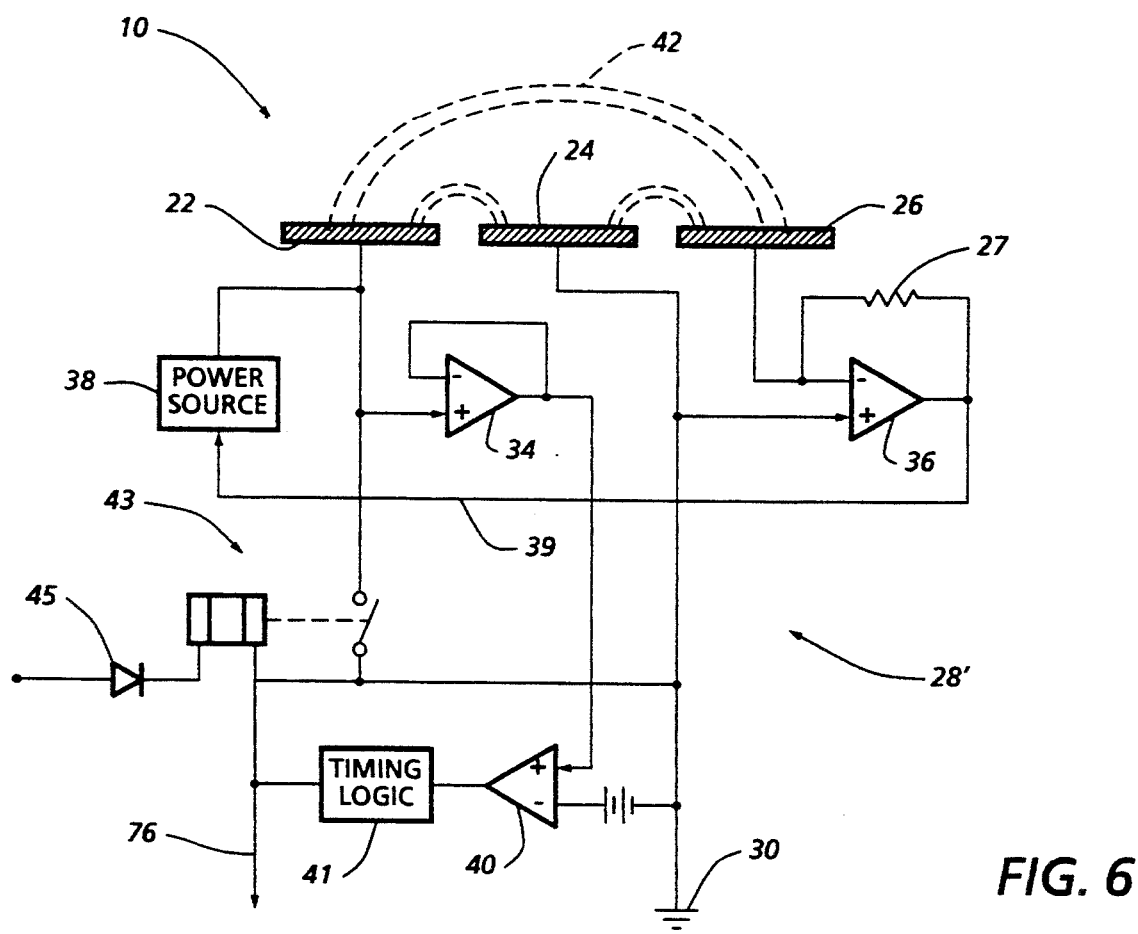
FIG. 6 is a circuit diagram of one of the probe receiving circuits depicted in FIG. 1, according to one embodiment of the invention.

An inexpensive type of probe receiver arrangement 28' as a replacement for the circuit 28 and impedance analyzer 32 hereinbefore described, is diagrammed in FIG. 6 according to another embodiment of the invention. The active electrodes 22 and 26 are respectively connected to the positive and negative input terminals of a voltage follower 34 and a current follower 36 The electrode 22 is also Connected to the output of a constant current electrical power source 38 having a feedback terminal connected to a feedback line 39 to sense the current conducted from the output of current follower 36 to electrode 26 and insert after "26". The output of voltage follower 34 is applied to one terminal of a comparator 40 having a reference voltage applied to its other terminal. The output of comparator 40 is connected to timing logic 41 for controllably energizing the coil of a start/stop relay 43 (or other switching means) through which the electrode 22 may be grounded by connection to the grounded electrode 24 as also shown in FIG. 6. The relay coil is also connected through diode 45 to the sensitivity selector 66 for purposes hereinbefore described.

Figure 7:
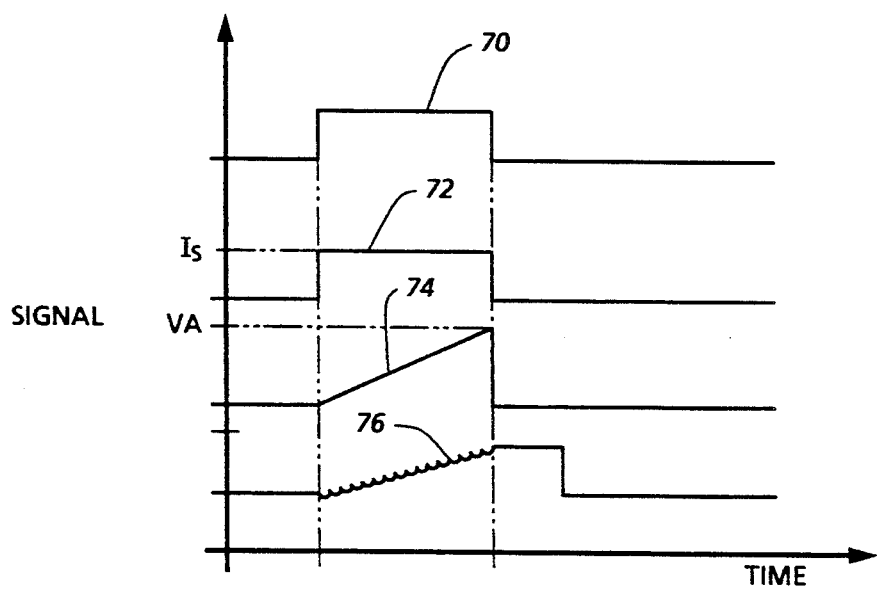
FIG. 7 is a graphical timing diagram characterizing operation of the probe circuits depicted in FIGS. 1 and 6.

Thus, in response to a command signal 70 applied to relay 43 as diagrammed in FIG. 7, the probe unit is enabled by opening of the relay switch to measure low frequencies in terms of time required for the output 74 of voltage follower 34 to reach a predetermined voltage $V_A$ due to the charging of the mutual capacitance between electrodes 22 and 26 by the current source 38, which is controlled through feedback line 39 to maintain a constant current 72 ($I_B$) conducted to electrode 26 as also diagrammed in FIG. 7. As a result of the foregoing operational process of the probe receiver 28' the output 76 of its counter logic 41 as shown in FIG. 6 provides a capacitive readout in a manner similar to the impedance analyzer 32 for the probe circuit 28 as hereinbefore described.

Also in connection with the circuitry of probe receiver 28', the relay 43, power source 38 and diode 45 are separately and simply depicted in FIG. 6 for illustrative purposes. The functions of such components may of course be implemented in a more integrated fashion through solid-state electronics.

Numerous other modifications and variations of the present invention are possible in light of the foregoing teachings. It is therefore to be understood that within the scope of the appended claims the invention may be practiced otherwise than as specifically described.

I claim:

1. Apparatus for measuring properties of a substance, comprising: a plurality of pairs of measuring electrodes spaced from said substance; electrically grounded guard electrodes respectively positioned each of the measuring electrodes of said pairs; a power source supplying driving current to one of the measuring electrodes of each of said pairs; switching means for selectively connecting said one of the measuring electrodes of each of said pairs respectively to said guard electrodes and means operatively connected to the switching means and the other of the measuring electrodes of each of said pairs for simultaneously analyzing impedances of the substance between the measuring electrodes of each pair.

2. Apparatus for measuring properties of a dielectric material having at least two pairs of measuring electrodes spaced by a lift-off distance from the dielectric material, the improvement residing in; and, restrictively positioned centrally between the measuring electrodes of each of said pairs and a probe circuit connected to each of said pairs of the electrodes, including: a power source, means operatively connecting the power source to one of said measuring electrodes of each of said pairs for supply of current thereto and switching means selectively connecting each of the guard electrodes to said one of said measuring electrodes for limiting said supply of the current to measurement intervals; and analyzer means operatively connected to the other of the measuring electrodes in each of the probe circuits for simultaneous measurements of impedances of the dielectric material between the measuring electrodes thereof during said measurement intervals.

3. The improvement as defined in claim 2, further including sensitivity selector means operatively connected to the probe circuit means for controlling operation of the switching means in accordance with differential weighting between said measurements of the impedances by the analyzer means.

4. Apparatus for measuring properties of a substance as a function of mutual capacitance between at least two pairs of measuring electrodes spaced by a lift-off distance from the substance, the improvement residing in: an electrically grounded guard electrode restrictively positioned centrally between the measuring electrodes of each of said pairs and a probe circuit connected to each of said pairs of the electrodes, including: a power source, means operatively connecting the power source to one of said measuring electrodes of each of said pairs for supply of current thereto, switching means selectively connecting each of the guard electrodes to one of the measuring electrodes in each of the pairs for limiting said supply of the current to measurement intervals, analyzer means operatively connected to the probe circuits for measurements of impedances of the substance between the measuring electrodes in response to outputs from the other of the measuring electrodes during said measurement intervals and sensitivity selector means operatively connected to the probe circuits for controlling operation of the switching means in accordance with differential weighting of said measurements of the impedances to determine said mutual capacitance of the substance.

5. The apparatus as defined in claim 1 wherein the power source connected to said one of the measuring electrodes results in a measurable signal at the other of the measuring electrodes of each of said pairs as a function of the impedances of the substance between the electrodes of each pair.

6. The apparatus as defined in claim 5 wherein said means for simultaneously analyzing the impedances includes current follower means connected to the other of the measuring electrodes of each pair and the guard electrodes for sensing the measurable signal.

* * * * *